United States Patent [19]
Metz et al.

[11] Patent Number: 5,831,137
[45] Date of Patent: Nov. 3, 1998

[54] PROCESS FOR THE PREPARATION OF ALKYL HALIDES

[75] Inventors: Josef Metz, Marl; Clemens Osterholt, Dorsten, both of Germany

[73] Assignee: Huels Aktiengesellschaft, Marl, Germany

[21] Appl. No.: 799,043

[22] Filed: Feb. 10, 1997

[30] Foreign Application Priority Data

Feb. 8, 1996 [DE] Germany ................. 196 04 568.1

[51] Int. Cl.⁶ ............................ C07C 17/02; C07C 17/08
[52] U.S. Cl. ........................... 570/246; 570/164; 570/251
[58] Field of Search .................................. 570/164, 246, 570/251

[56] References Cited

U.S. PATENT DOCUMENTS 2,389,230  11/1945  Blumer ................................ 570/246

FOREIGN PATENT DOCUMENTS 669 733  1/1966  Belgium .
665 809  1/1952  United Kingdom .

*Primary Examiner*—Alan Siegel
*Attorney, Agent, or Firm*—Oblon, Spivak, McClelland, Maier & Neustadt, P.C.

[57] ABSTRACT

In the continuous preparation of alkyl halides from branched olefins and hydrohalic acids, the reaction is carried out without the addition of catalysts and without solvents. With a high olefin conversion, alkyl halides are obtained with high selectivity and with very good color quality.

17 Claims, 2 Drawing Sheets

PROCESS FOR THE PREPARATION OF ALKYL HALIDES

BACKGROUND OF THE INVENTION

1. Field of the Invention

The invention relates to a novel process for the continuous preparation of alkyl halides from branched olefins having 4 to 16 carbon atoms and concentrated hydrohalic acid.

2. Discussion of the Background

Alkyl halides are used as solvents. They are additionally employed for Friedel-Crafts alkylations, for the preparation of organometallic compounds and for the synthesis of plant protection products and pharmaceuticals.

The preparation of alkyl halides generally starts from alcohols or from olefins. In U.S. Pat. No. 3,852,368, tert-alkyl chlorides are prepared in solvents, such as pentane, hexane, carbon tetrachloride or benzene, in the presence of tertiary amines in aqueous hydrochloric acid at low temperatures. U.S. Pat. No. 2,434,092 describes the preparation of alkyl halides in the presence of $BF_3$, or $BF_3$ adducts, as catalysts. These processes are inelegant and/or complex, because the solvents must be separated off and the catalysts must be worked up.

SUMMARY OF THE INVENTION

An object of the present invention is to provide a simple process for the preparation of alkyl halides from olefins.

This object is achieved by a process comprising reacting an olefin with a haloacid without the addition of a catalyst or solvents.

DETAILED DESCRIPTION OF THE INVENTION

Olefins for use in the present invention preferably have 4 to 16 carbon atoms, and are preferably branched. More preferably the olefins having 4 to 8 carbon atoms. Examples of suitable branched olefins are isobutene, 2-methylbut-2-ene, 3-methylpent-2-ene, 2,3-dimethylbut-2-ene, 2,3-dimethylpent-2-ene, 2-ethylhex-2-ene, 2-methyloct-1-ene, 2,4-dimethyldec-1-ene and isoprene.

Suitable hydrohalic acids are hydrochloric, hydrobromic and hydroiodic acid. Concentrated hydrohalic acids within the meaning of the present invention are at least 20% strength hydrohalic acids in water. Concentrated hydrochloric acids are preferably from 20 to 45% in strength. All strengths of hydrohalic acids are weight percentages, in waters, unless otherwise specified.

The process of the present invention is preferably used to prepare tertiary alkyl chlorides.

The reaction temperature is not critical. It is generally in the range from 0° to 200° C. Below this range, the reaction is slow and in some cases incomplete. Above 200° C., product discoloration tends to occur more frequently. The reaction temperature is preferably in the range of from 20° to 160° C. Where a continuous reaction is carried out at a temperature above the boiling point of the alkyl halide, the safety-related expenditure is comparatively low. This is the case, for example, if tert-butyl chloride, having a boiling point of 51° C., is prepared at a reaction temperature of 60° C.

A general advantage of the process of the present invention is that the reaction can be carried out under atmospheric pressure. Surprisingly, this process produces alkyl halides with high olefin conversions, in high purity and high selectivity, and with very good color. Consequently, only very simple distillative purification operations are required, if any, in order to further improve the color. Furthermore, there is no need to handle any catalysts.

In the context of the present invention, a solvent is an organic solvent present at more than 10% by weight, preferably at more than 5% by weight, more preferably 1% by weight, which does not react or form during the process, and is not a standard additive in one of the reactants, or impurity. For example, water present in the concentrated hydrohalic acid is not a solvent.

Having generally described this invention, a further understanding can be obtained by reference to certain specific examples which are provided herein for purposes of illustration only and are not intended to be limiting unless otherwise specified.

EXAMPLES

Example 1

Figure 1:
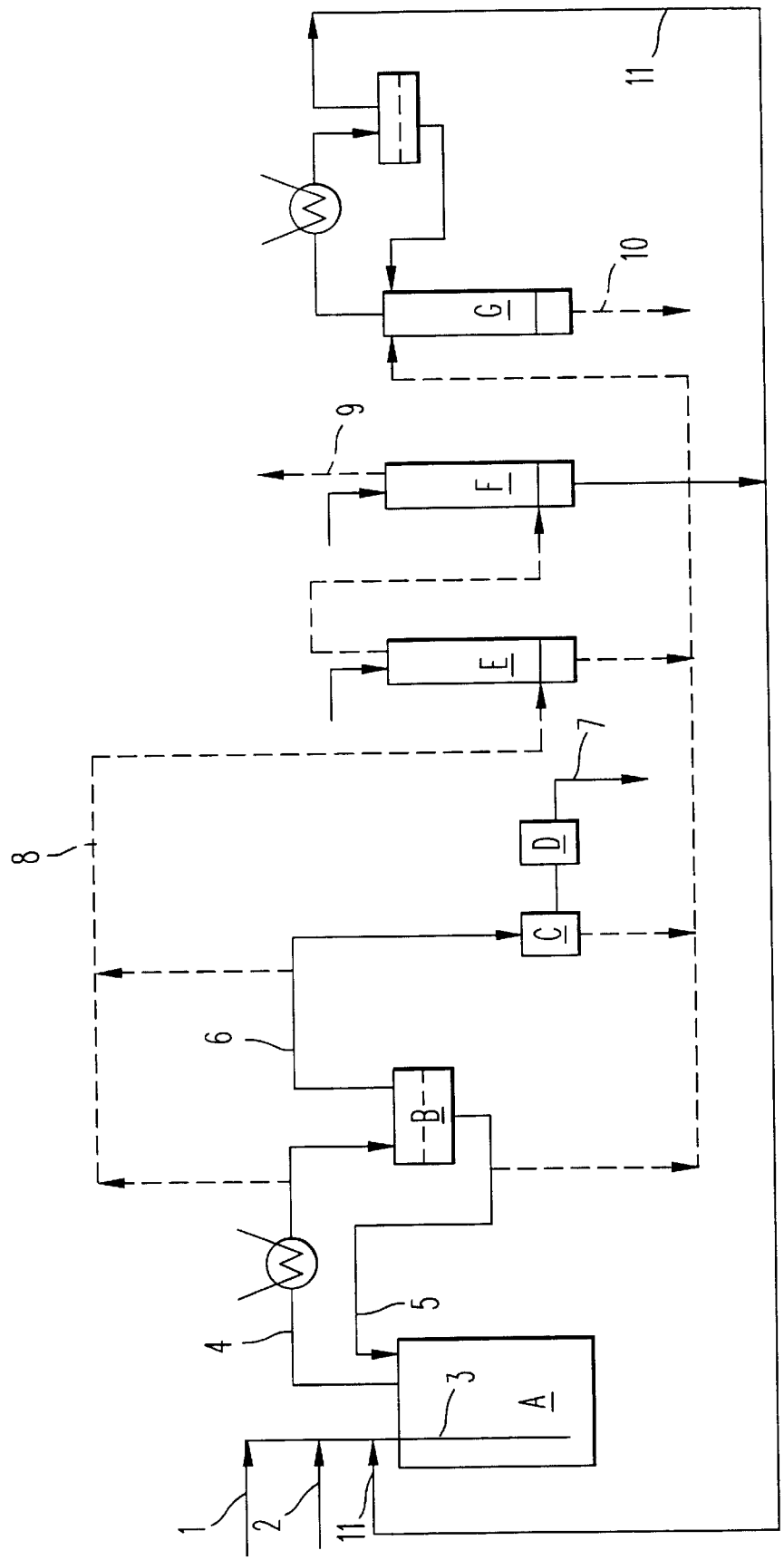
FIG. 1 is a schematic of an apparatus and steps described in Example 1.

Continuous Preparation of tert-butyl chloride (FIG. 1)

1.5 kg of concentrated hydrochloric acid (about 35% strength) are initially introduced into a glass reactor (A) blanketed with $N_2$. This initial charge is brought to 60° C., and a mixture of 1 mol of isobutene (1) and about 1.2 mol of hydrogen chloride (2) are passed in hourly, via a dip tube (3) which is fitted at the bottom end with a glass frit, in order to distribute the gas more effectively.

The reaction product which is obtained in this reactor is drawn off in vapor form (4) and condensed, and the two-phase distillate in the receiver (B) is separated.

The lower, aqueous phase is recycled (5) and the upper, alkyl chloride phase (6) may then be worked up [alkaline scrubbing (C) and alkaline drying (D)].

The tert-butyl chloride (7) thus prepared is obtained with a yield of >95% of theoretical predictions, based on the olefin. The purity by gas chromatography (GC) analysis is >99.8%; APHA color number ≦10; and an $H_2O$ content ≦300 ppm. The off-gas, predominantly hydrogen chloride and nitrogen, with a small amount of isobutene and tert-butyl chloride, is passed via the collection line (8) to the $H_2O$ countercurrent scrubber (E) for absorption of HCl and then to the tert-butanol countercurrent scrubber (F) for absorption of alkyl chlorides. The cleaned off-gas (9) can be passed to a disposal unit, for example a waste-gas incinerator. The tert-butanol from the countercurrent scrubber (F), which is enriched with tert-butyl chloride, is fed back into the reactor (A).

The process waste waters are adjusted to a pH of <7 and are passed to the stripping column (G) in order to remove organic constituents. The upper, organic phase of the azeotrope produced (predominantly olefins, alkyl chlorides, alcohols and aqueous hydrochloric acid) is recycled to the reactor (A), and the lower, aqueous azeotrope phase is run into the upper section of the stripping column. The bottom product (10), which has been freed from organic fractions, is passed to a waste water treatment plant.

Example 2

Figure 2:
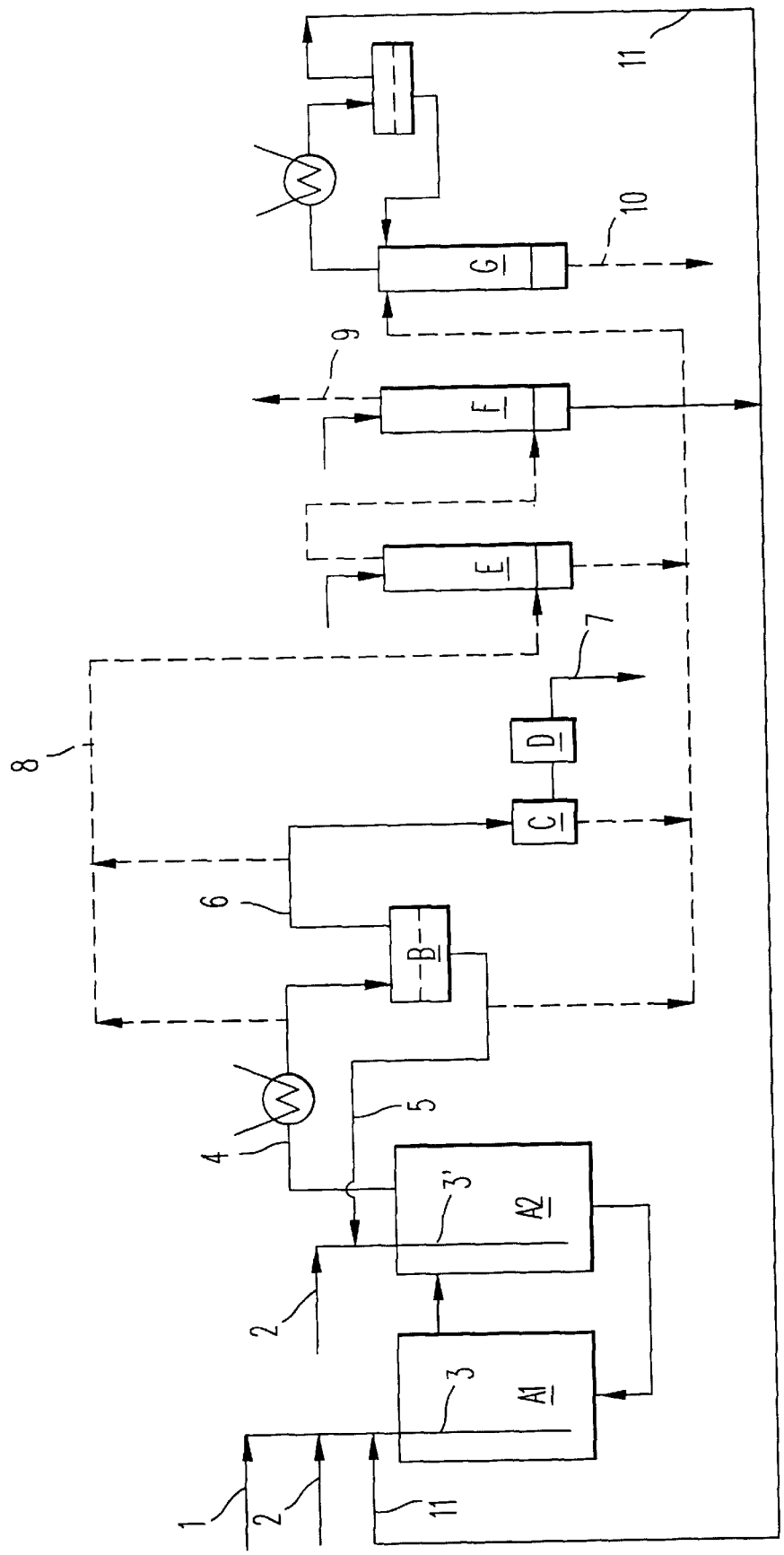
FIG. 2 is a schematic of an apparatus and steps described in Examples 2 and 3.

Continuous preparation of tert-amyl chloride (FIG. 2)

Two glass reactors in series ($A_1$ and $A_2$) are filled with about 2 kg each of concentrated hydrochloric acid (about 36% strength). Reactor $A_1$ is adjusted to 30° C. and reactor A₂ to 90° C. A mixture of about 1 mol of 2-methylbut-2-ene (97.7% strength) and about 1 mol of hydrogen chloride is passed hourly, via the dip tube (3) into reactor A₁. The reaction product passes via an overflow into reactor A₂. In this reactor, an additional 0.3 mol of hydrogen chloride (2') is metered in, and the reaction product is drawn off via the top (4). The condensed, two-phase distillate is separated in the receiver B. The reaction is subsequently worked up as in Example 1. The countercurrent scrubber (F) is operated with 2-methylbutan-2-ol.

In this cascade procedure, the conversion of olefin in the first reactor is >95%, with the remaining conversion taking place in the second reaction stage. The tert-amyl chloride (7) thus prepared is obtained with a yield of >95% of theoretical predictions. The purity by GC analysis is 98.0%; APHA color number ≦10; H₂O content ≦200 ppm.

Example 3
Continuous preparation of tert-hexyl chloride (FIG. 2)

Two glass reactors in series (A₁ and A₂) are filled with about 2 kg each of concentrated hydrochloric acid (about 36% strength). Reactor A₁ is adjusted to 40° C. and reactor A₂ to 105° C. A mixture of about 1 mol of 3-methylpent-2-ene (cis/trans content 88%, 2-ethylbut-1-ene=12%) and about 1 mol of hydrogen chloride (2) is passed hourly, via the dip tube (3) into reactor A₁.

The reaction product passes via an overflow into reactor A₁. In this reactor, an additional 0.3 mol of hydrogen chloride (2') is metered in, and the reaction product is drawn off as an azeotrope via the top (4). The condensed, two-phase distillate is separated in the receiver B. The reaction is subsequently worked up as in Example 1. The countercurrent scrubber (F) is operated with 3-methylpentan-3-ol.

In this cascade procedure, the conversion of olefin in the first reactor is about 93%, with the remaining conversion taking place in the second reaction stage. The tert-hexyl chloride (7) thus prepared is obtained with a yield of >95% of theoretical predictions. The purity by GC analysis is 98.7%; APHA color number is 30; and H₂O content <200 ppm.

Obviously, additional modifications and variations of the present invention are possible in light of the above teachings. It is therefore to be understood that within the scope of the appended claims, the invention may be practiced otherwise than as specifically described herein.

The priority document of the present application, German patent application 196 04 568.1, filed Feb. 8, 1996, is hereby incorporated by reference.

What is claimed as new and desired to be secured by Letters Patent of the United States is:

1. A process for the preparation of alkyl halides, comprising:
    reacting at atmospheric pressure in the absence of a catalyst and solvent a branched olefins having 4–16 carbon atoms with an at least 20% by weight strength of a concentrated hydrohalic acid in water.

2. The process of claim 1, wherein the olefin has 4–8 carbon atoms.

3. The process of claim 1, wherein the reacting is carried out at a temperature of from 20°–160° C.

4. The process of claim 1, wherein the process produces a tertiary alkyl chloride.

5. The process according to claim 1, comprising:
    adding at atmospheric pressure an olefin and a hydrogen halide to an at least 20% by weight strength concentrated hydrohalic acid in water, thereby forming an alkyl halide.

6. The process of claim 5, wherein said concentrated hydrohalic acid is hydrochloric acid.

7. The process of claim 5, wherein said olefin is a branched olefin having 4–16 carbon atoms.

8. The process of claim 5, wherein the olefin has 4–8 carbon atoms.

9. The process of claim 5, wherein said alkyl halide is a tertiary alkyl chloride.

10. The process of claim 5, further comprising:
    removing said alkyl halide from said concentrated hydrohalic acid as a vapor.

11. The process of claim 10, wherein said adding and said removing are carried out simultaneously.

12. The process of claim 11, wherein said adding and said removing are carried out continuously for at least one hour.

13. The process according to claim 5, comprising:
    adding said olefin and hydrogen halide to a first container containing a first liquid comprising said concentrated hydrohalic acid, thereby forming an alkyl halide; and
    transferring a portion of said liquid to a second container containing a second liquid comprising said concentrated hydrohalic acid.

14. The process of claim 13, wherein said olefin is a branched olefin having 4–16 carbon atoms.

15. The process of claim 13, further comprising:
    removing said alkyl halide from said second container as a vapor;
    wherein said adding, said transferring and said removing are carried out simultaneously and continuously for at least one hour.

16. The process of claim 15, wherein said first and second liquids are at a temperature of 20°–160° C., and the temperature of said first liquid is lower than the temperature of said second liquid.

17. The process according to claim 1, wherein said concentrated hydrohalic acid is concentrated hydrochloric acid.

* * * * *